United States Patent
Stefanson et al.

(10) Patent No.: US 9,167,882 B2
(45) Date of Patent: Oct. 27, 2015

(54) TOOTHBRUSH WITH INTERDENTAL BRUSH STORAGE

(71) Applicant: Import Partners, Inc., Fridley, MN (US)

(72) Inventors: Michael Joseph Stefanson, Arden Hills, MN (US); Richard Joseph Mrocek, North Oaks, MN (US)

(73) Assignee: Import Partners, Inc., Fridley, MN (US)

( * ) Notice: Subject to any disclaimer, the term of this patent is extended or adjusted under 35 U.S.C. 154(b) by 0 days.

(21) Appl. No.: 14/213,431

(22) Filed: Mar. 14, 2014

(65) Prior Publication Data

US 2015/0257519 A1 Sep. 17, 2015

(51) Int. Cl.
| | |
|---|---|
| *A45D 44/18* | (2006.01) |
| *A46B 11/00* | (2006.01) |
| *A46B 15/00* | (2006.01) |
| *A61C 15/00* | (2006.01) |
| *A61C 15/04* | (2006.01) |

(52) U.S. Cl.
CPC .............. *A45D 44/18* (2013.01); *A46B 15/00* (2013.01); *A46B 15/0071* (2013.01); *A46B 2200/108* (2013.01); *A61C 15/046* (2013.01)

(58) Field of Classification Search
CPC ...... A46B 5/0004; A46B 5/00; A46B 5/0016; A46B 15/0095; A46B 15/00; A46B 15/0069; A46B 15/0071; A46B 15/0055; A46B 2200/1066; A46B 2200/108; A46B 2200/1086; A46B 2200/405; A46B 2200/10; A61C 15/00; A61C 15/04; A61C 15/043; A61C 15/046; A61C 17/222; A61C 17/225; A61C 19/02; A45D 44/18

USPC ........ 132/310, 308, 309, 311, 321, 328, 329; 15/22.1, 106, 167.1, 110, 111, 184; 206/581, 823, 368, 369, 63.5; 433/141; 606/161

See application file for complete search history.

(56) References Cited

U.S. PATENT DOCUMENTS

| | | | | | |
|---|---|---|---|---|---|
| 1,419,887 | A | * | 6/1922 | Myers | 15/184 |
| 1,495,675 | A | * | 5/1924 | Colt | 132/309 |
| 2,105,709 | A | * | 1/1938 | Violette | 222/512 |
| 2,468,298 | A | * | 4/1949 | Kahn | 132/309 |
| 2,624,062 | A | * | 1/1953 | Knoderer | 15/167.1 |
| 2,640,488 | A | * | 6/1953 | Velodota | 132/308 |
| 2,651,070 | A | * | 9/1953 | Zimmerman | 15/185 |
| 2,800,899 | A | * | 7/1957 | Barron | 601/141 |

(Continued)

FOREIGN PATENT DOCUMENTS

| | | |
|---|---|---|
| EP | 0193101 B1 | 4/1990 |
| KR | 200407689 | 2/2006 |

(Continued)

*Primary Examiner* — Vanitha Elgart
(74) *Attorney, Agent, or Firm* — Schwegman Lundberg & Woessner, P.A.

(57) ABSTRACT

A dental hygiene device includes a toothbrush component and at least one interdental brush component that can be stored within the toothbrush component. At least one ventilation window located within the toothbrush component allows for drying of the interdental brush component to prevent the growth of biofilms. The interdental brush component removably attaches to the toothbrush component by a latch mechanism, a door mechanism or a friction fit between the interdental brush component and the toothbrush component.

11 Claims, 5 Drawing Sheets

(56) References Cited

U.S. PATENT DOCUMENTS

| | | | |
|---|---|---|---|
| 3,088,645 A * | 5/1963 | Mechaneck | 206/361 |
| 4,296,518 A * | 10/1981 | Furrier et al. | 15/110 |
| 4,691,404 A | 9/1987 | Tarrson et al. | |
| D296,271 S * | 6/1988 | Kobayashi | D4/108 |
| 5,046,212 A | 9/1991 | O'Conke | |
| 5,097,852 A | 3/1992 | Wu | |
| 5,205,302 A * | 4/1993 | Lemon et al. | 132/321 |
| 5,967,152 A * | 10/1999 | Rimkus | 132/308 |
| 6,015,293 A * | 1/2000 | Rimkus | 433/141 |
| 6,220,773 B1 * | 4/2001 | Wiegner et al. | 401/195 |
| 6,247,477 B1 * | 6/2001 | Wagner | 132/309 |
| 6,957,467 B2 * | 10/2005 | Cabedo-Deslierres et al. | 15/106 |
| 2002/0073496 A1 * | 6/2002 | Kim | 15/106 |
| 2005/0211263 A1 * | 9/2005 | Kuo | 132/310 |
| 2006/0269351 A1 * | 11/2006 | McAfee | 401/125 |
| 2009/0200184 A1 * | 8/2009 | Cullen | 206/362.2 |

FOREIGN PATENT DOCUMENTS

| | | |
|---|---|---|
| KR | 200426833 | 9/2006 |
| WO | WO-2006022485 A1 | 3/2006 |
| WO | WO-2009011548 A1 | 1/2009 |

* cited by examiner

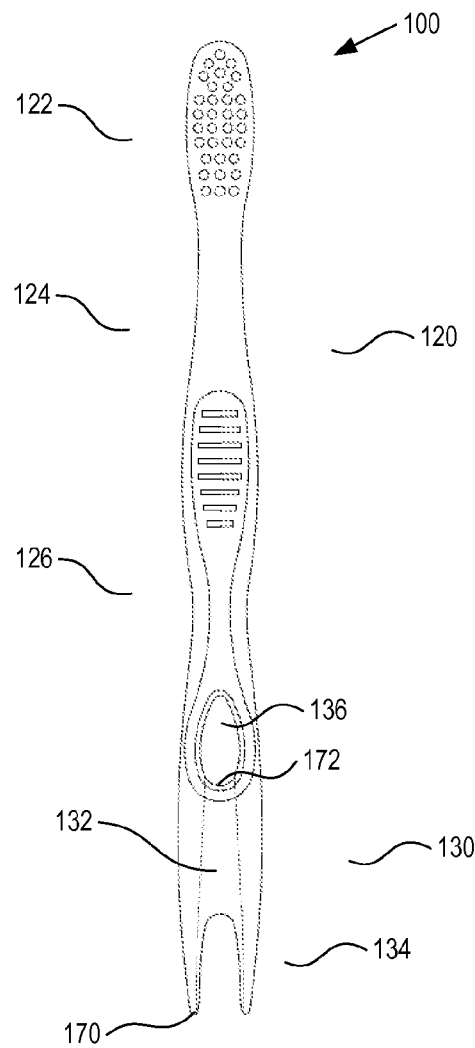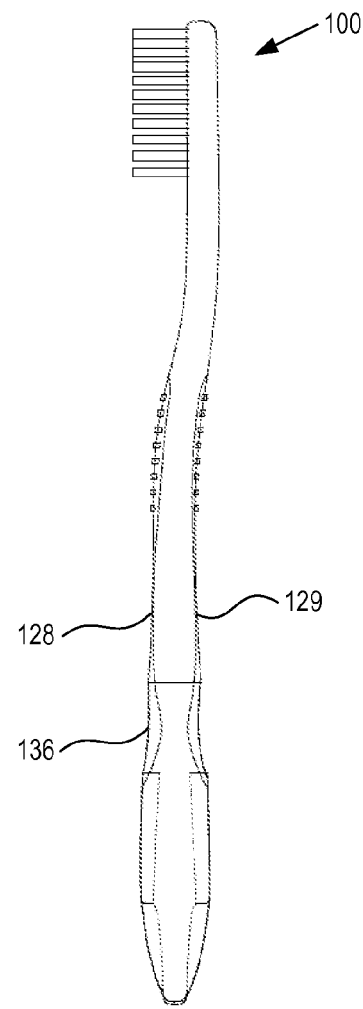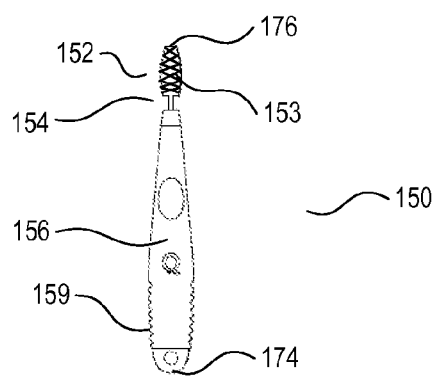
FIG. 1A　　　　　　　　　　FIG. 1B

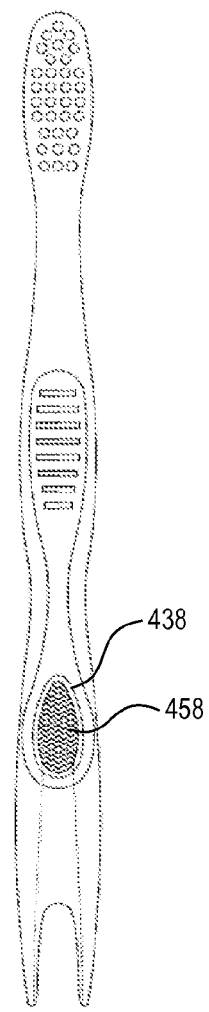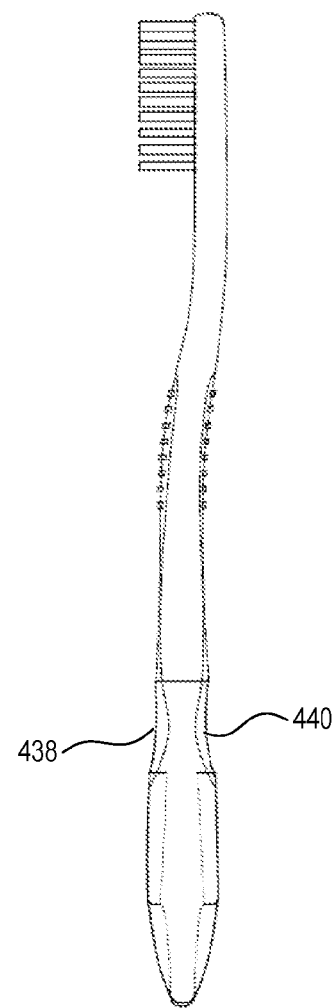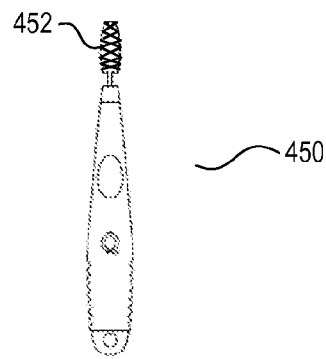
FIG. 4A
FIG. 4B

TOOTHBRUSH WITH INTERDENTAL BRUSH STORAGE

BACKGROUND

Periodontal disease is a condition of the mouth that can result in tooth loss and has been associated with other chronic ailments such as heart disease, stroke and diabetes. The most common forms of periodontal disease are gingivitis (an inflation of the gum tissue) and periodontitis (an inflation of the periodontium, or the tissues that surround and support the teeth) that are associated with the growth of biofilms in the mouth. The act of brushing one's teeth with a toothbrush or similar device can effectively clean biofilms from the outward facing surfaces of the teeth, but will not reach the areas between the teeth otherwise known as interdental spaces. To prevent periodontal disease, dentists and dental hygienists strongly recommend that patients floss to clean interdental spaces in conjunction with regular brushing.

However, many patients resist the admonition to floss regularly. Many reasons have been cited for failure to comply with flossing recommendations, such as the inconvenience of flossing. Some dentists recommend interdental brushes for better cleaning of interdental spaces. However, patients resist that practice as yet another time-consuming step in dental care. Some of the reasons offered include the extra time it takes to locate the interdental brushes and problems that come with handling the small interdental brushes.

What is needed in the art is a dental brush with a conveniently accessible compartment for storing an interdental brush.

OVERVIEW

A dental hygiene device includes a toothbrush component and at least one interdental brush component that can be stored within the toothbrush component. At least one ventilation window located within the toothbrush component allows for drying of the interdental brush component to prevent the growth of biofilms. The interdental brush component removably attaches to the toothbrush component by a latch mechanism, a door mechanism or a friction fit between the interdental brush component and the toothbrush component.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components.

FIG. 1A is a front view of an example dental hygiene device with at least one ventilation hole as described in the disclosure.

FIG. 1B is a side view of an example dental hygiene device with at least one ventilation hole as described in the disclosure.

FIG. 4A is a front view of an example dental hygiene device with example grids covering two ventilation holes as described in the disclosure.

FIG. 4B is a side view of an example dental hygiene device with example grids covering two ventilation holes as described in the disclosure.

DETAILED DESCRIPTION

Figure 2A:
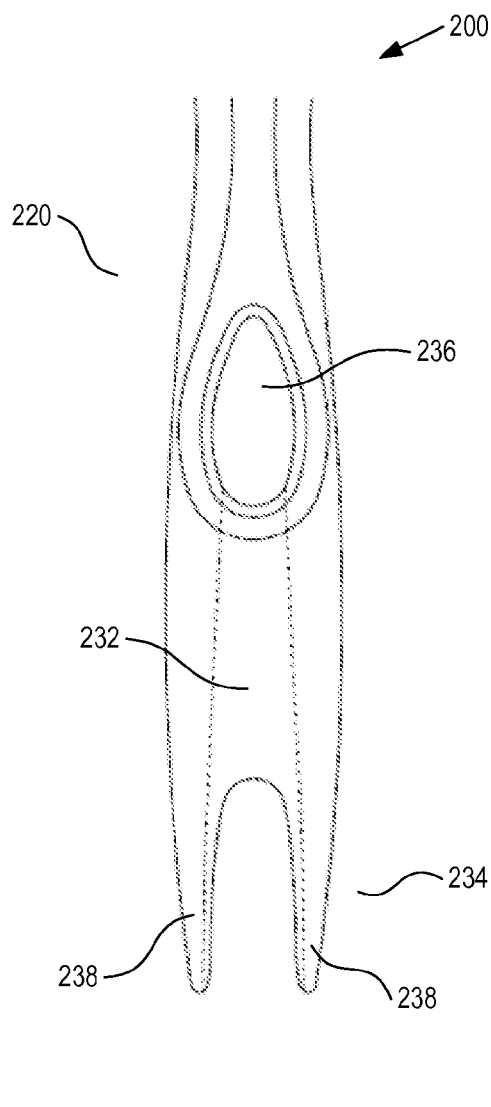
FIG. 2A is a front view (left) of a segment of an example dental hygiene device illustrating a two-lobe connection portion.

FIGS. 1A and 1B show an example dental hygiene device 100 of the present disclosure. The dental hygiene device 100 comprises a toothbrush component 120 and an interdental brush storage portion 130 with a distal end 170 and a proximal end 172 adapted to hold at least one interdental brush 150. The toothbrush component 120 includes a front surface 128 and a rear surface 129 and comprises a brush portion 122, a neck portion 124, and a handle portion 126. The interdental brush storage portion 130 further comprises a recess 132 including a connection portion 134 and at least one ventilation hole 136 in communication with the recess 132.

The interdental brush component 150 includes a distal end 174 and a proximal end 176 and comprises a bristle portion 152, a column portion 154 and a grip 156.

The bristle portion 152 can be inserted into the interdental spaces of a user's teeth to remove debris from the interdental spaces. The bristle portion 152 can comprise a plurality of bristle filaments 153 where the composition of the filaments can include, but is not limited to, polymer fibers, natural fibers or a combination of polymer and natural fibers. The bristle portion 152 can assume any volumetric shapes without altering the effect of the interdental brush 150 including, but not limited to, a cone, a cylinder, a pyramid or any bilaterally or non-bilaterally symmetric shape. As used here, the term volumetric shape can include any three-dimensional structure or the volumetric envelope formed by revolving any two-dimensional structure about a specified axis. The filaments 153 can be secured to the column portion 154 by a variety of methods including, but not limited to, gluing, melting, welding, flocking or interference fit.

The column portion 154 connects the bristle portion 152 to the grip 156. The column portion 154 can comprise at least one cable of a polymer material, at least one wire of a metal material, at least one wire of a metal material coated with at least one polymer material or a combination of cables or wires of polymer materials, metal materials, or metal materials coated with at least one polymer material. In an example, the filaments 153 can be connected to the column portion 154 by twisting. As used here, the term twisting can comprise generally folding a length of wire to form a column portion 154 with two legs, locating bristle filaments 153 between the two legs along the length of the legs and twisting the column portion 154 so that the filaments 153 are secured between the legs of the column portion 154.

The grip 156 can provide at least one surface that a user can grasp when inserting the interdental brush 150 into the interdental spaces of the user. The grip 156 can be made from any material without altering the effect of the grip 156 including, but not limited to, polymer materials with different durometer ratings. In an example, a portion of the grip 156 can be made from a polymer of a first durometer rating and a different portion of the grip 156 can be made from a polymer of a second durometer rating where the first and second durometer ratings are not equal. The grip 156 can assume any shape without altering the effect of the grip 156 including, but not limited to, a generally elongated cone shape. In an example, the grip 156 can assume a shape compatible with the shape of the recess 132 to create an interference fit between the grip 156 and the recess 132 and thereby removably retain the interdental brush 150 within the recess 132. In an example, the grip 156 can include ribs 159 to create an interference fit between the grip 156 and the connection portion 134 and thereby removably retain the interdental brush 150 within the recess 132.

In an example, the recess 132 is adapted to accommodate an interdental brush 150 designed and manufactured specifically for use in combination with the dental hygiene device 100. In another example, the recess 132 is adapted to accommodate interdental brushes commercially available from other manufacturers.

In an example, the interdental brush component 150 can be removably attached to the toothbrush component 120 by locating the interdental brush component 150 in the recess 132 of the toothbrush component 120. In some examples, the interdental brush 150 can be retained in the recess 132 by a latch mechanism, a door mechanism. In some examples, the interdental brush 150 can be retained in the recess 132 by a friction fit mechanism between the grip 156 and a portion of the recess 132, between the grip 156 and the connection portion 134 or between the grip 156 and a combination of the recess 132 and the connection portion 134. As used here, the term friction fit can include an interference fit, a press fit or any other intimate contact between two surfaces where friction is generated by virtue of interaction between the two surfaces to maintain the fit. Other types of attachments may be employed without departing from the present subject matter. Depending on the amount of force a user employs to establish removable attachment between the grip 156 and the recess 132, the dimensional tolerances of the components used and other parameters, the user may find it difficult to detach the interdental brush 150 from the recess 132. Proper design of the recess 132 and the grip 156 can mitigate potential usability issues.

In an example, the recess 132 can assume a tapered configuration from a distal end 170 to a proximal end 172 and the grip 156 can assume a similarly tapered configuration from a distal end 174 to a proximal end 176 such that when the interdental brush 150 is inserted into the recess 132, the outer surface of the grip 156 can intimately contact a portion of the recess 132. In an example, the connection portion 134 can substantially contact the entire outer surface of the grip 156. In an example, the connection portion 134 can substantially contact less than the entire outer surface of the grip 156. In an example, the outer surface of the grip 156 can be formed so that only desired portions of the outer surface of the grip 156 substantially contact the connection portion 134. In an example, the connection portion 134 can assume a configuration with one or more lobes so that the connection portion 134 substantially contacts less than the entire outer surface of the grip 156.

FIG. 2A illustrates a segment of an example dental hygiene device 200 where the connection portion 234 assumes a two-lobed configuration wherein each lobe 238 is generally symmetric and generally equally spaced around the periphery of the connection portion 234.

Figure 2B:
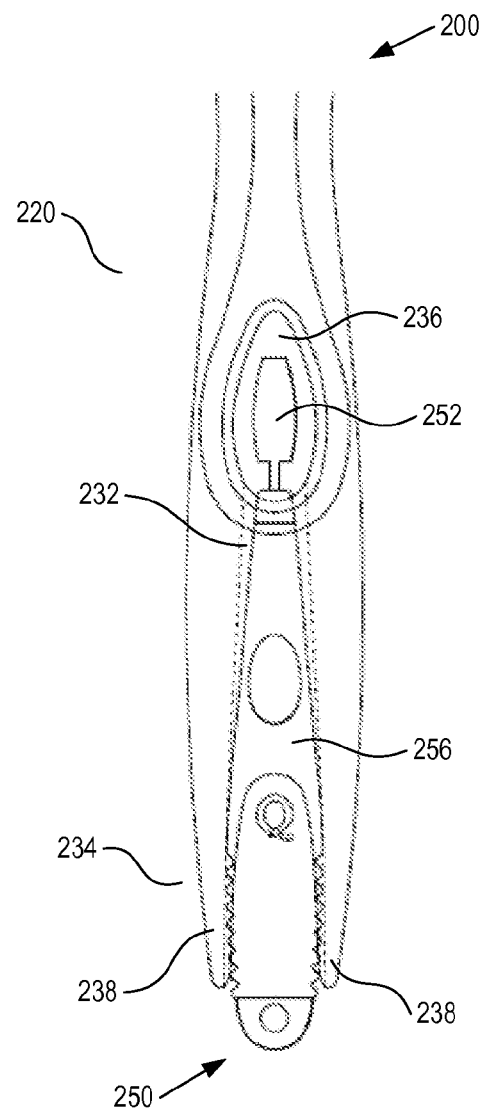
FIG. 2B is a front view of a segment of an example dental hygiene device illustrating a two-lobe connection portion with an interdental brush removably connected to the two-lobe connection portion.

FIG. 2B illustrates a segment of an example dental hygiene device 200 with an interdental brush 250 removably attached to the device 200. When the interdental brush 250 is inserted into the recess 232, the grip 256 can contact the two lobes 238 of connection portion 234 creating a friction fit between the lobes 238 and the grip 256. As compared to a device where the connection portion 234 can substantially contact the entire outer surface of the grip 256, the two-lobed configuration can allow a user greater access to the surface of the grip 256. For example, grasping the grip 256 with thumb and forefinger between the lobes 238 can allow for greater contact with the grip 256 and thus, easier extraction of the interdental brush 250 from the storage portion 230. In an example, the lobes 238 can assume various shapes including, but not limited to, circles, ovals, ellipses, squares, rectangles or other polygonal shapes. In an example, any other shapes and numbers of lobes are possible without departing from the scope of the present subject matter.

The toothbrush component 220 and the interdental brush component 250 are designed to clean the surfaces and interdental spaces of a user's teeth. As a result, the toothbrush 220 and interdental brush 250 are wetted with water and other bodily fluids during the course of use. To inhibit or prevent the growth of undesirable organisms or biofilms on the surfaces of the toothbrush 220 and interdental brush 250, it is desirable that the surfaces be allowed to dry. In an example, drying of the toothbrush 220 and interdental brush 250 surfaces can be achieved by evaporation of moisture or fluid from those surfaces into the ambient environment. For evaporation to occur, the toothbrush 220 and interdental brush 250 surfaces can be exposed to ambient air. In an example, the at least one ventilation hole 236 allows the bristle portion 252 of the interdental brush 250 to dry by exposing the interdental brush 250 to the ambient environment.

Figure 3A:
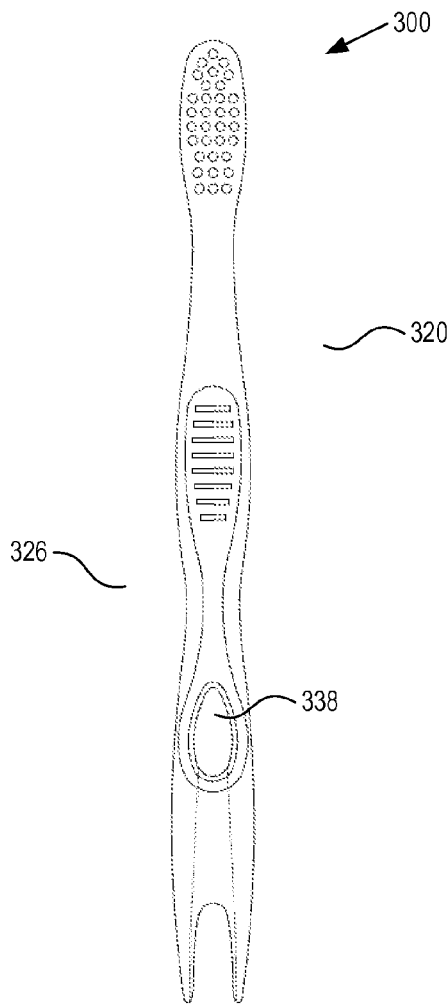
FIG. 3A is a front view of an example dental hygiene device with two ventilation holes as described in the disclosure.
Figure 3B:
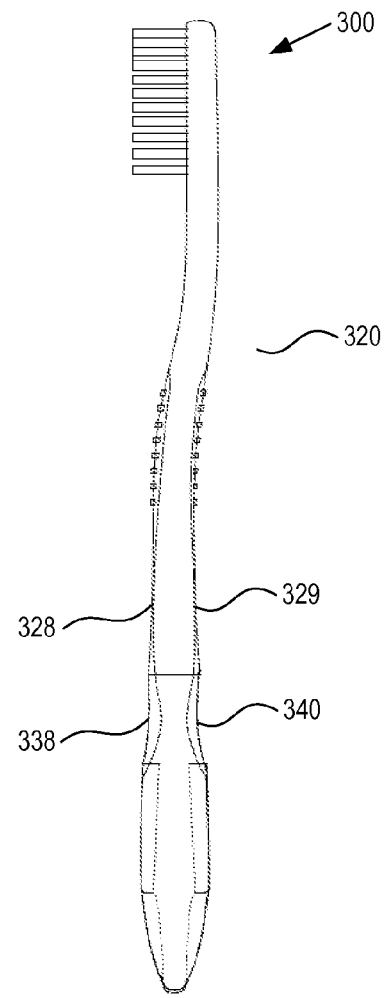
FIG. 3B is a side view of an example dental hygiene device with two ventilation holes as described in the disclosure.

FIGS. 3A and 3B show an example of the toothbrush component 320 with a first ventilation hole 338 in the front surface 328 of the handle portion 326 and a second ventilation hole 340 in the rear surface 329 of the handle portion 326. The combination of the first ventilation hole 338 and the second ventilation hole 340 allows air to flow freely from the front surface 328 to the rear surface 329 (or vice-versa) around the bristle portion 352 of interdental brush 350 to enhance evaporation from the bristle portion 352. In an example, an axis connecting the centroids of the first and second ventilation holes 338, 340 can be substantially perpendicular to the long axis of the dental hygiene device 300. In an example, an angle between an axis connecting the centroids of the first and second ventilation holes 338, 340 and the long axis of the dental hygiene device 300 can be acute or obtuse. In an example, the first and second ventilation holes 338, 340 can assume various shapes including, but not limited to, circles, ovals, ellipses, squares, rectangles or other closed polygonal shapes. In an example, other shapes and numbers of ventilation holes are possible without departing from the scope of the present subject matter.

As the planar surface area of the first and second ventilation holes 338, 340 increases, the volume of air that can pass through the first and second ventilation holes 338, 340 can increase and can result in accelerated drying of the bristle portion 352. In an example, the planar surface area of the first and second ventilation holes 338, 340 can occupy approximately 5% of the front and rear surface area 328, 329 respectively. In an example, the planar area of the first and second ventilation holes 338, 340 can occupy approximately 10%, 20%, 30% or more of the front and rear surface area 328, 329, respectively. In an example, the surface area of the first ventilation hole 338 can be different from the surface area of the second ventilation hole 340. In an example, the shape of the first ventilation hole 338 can be different from the shape of the second ventilation hole 340.

FIGS. 4A and 4B show an example of a first ventilation hole 438 that includes a first grid component 458 that substantially covers the first ventilation hole 438. As used in this disclosure, the term grid can include any mesh or otherwise organized framework of crisscrossed or substantially parallel members. The first grid component 458 can prevent foreign objects from touching or otherwise coming in contact with the bristle portion 452 of the interdental brush component 450 while presenting substantially the same surface area for drying as the first ventilation hole 438. The material of the first grid component 458 can include, but is not limited to a metal or polymer wire that has been formed in a drawing, casting or similar mesh production operation. In an example, the second ventilation hole 440 can include a second grid component similar in shape to the first grid component 458.

Figure 5:
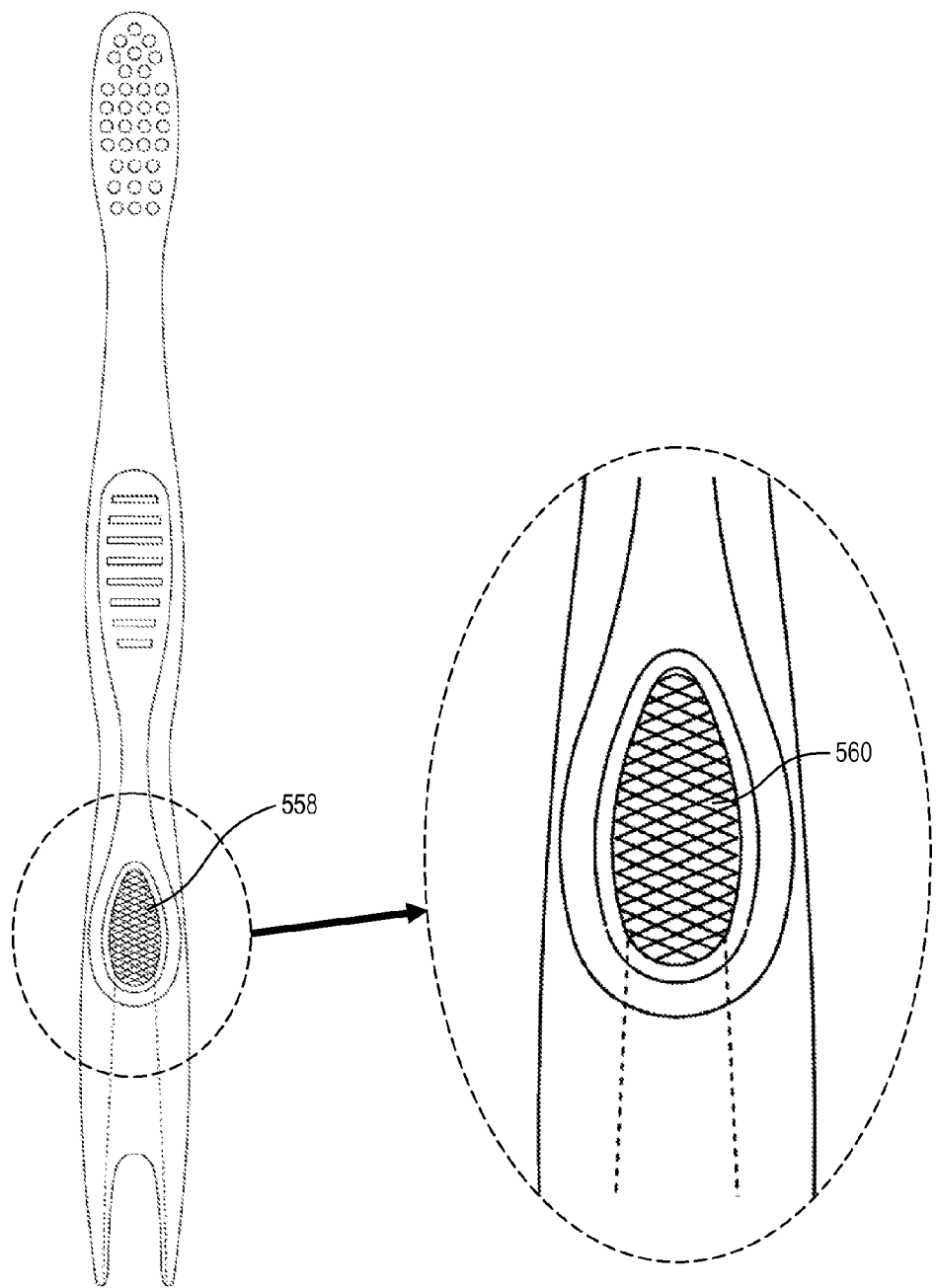
FIG. 5 is a front view of an example dental hygiene device and a close up an example grid covering a ventilation hole as described in the disclosure.

FIG. 5 shows a close up view of an example first grid component 558. In an example, the grid voids 560 can be a function of spacing between the various grid members. In an example the grid voids 560 can assume various planar shapes including, but not limited to, circles, ovals, ellipses, squares, rectangles or other closed polygonal shapes. In an example, other shapes and numbers of grid voids are possible without departing from the scope of the present subject matter.

The claimed invention is:

1. A dental hygiene device comprising:
a toothbrush component comprising a brush portion, a neck portion, and a handle portion, the handle portion including a front surface, a rear surface, and an interdental brush storage portion, the interdental brush storage portion including a recess adapted to accommodate an interdental brush, a connection portion, and at least one ventilation hole in communication with the recess,
wherein the at least one ventilation hole includes a first ventilation hole that extends through the front surface of the handle portion and a second ventilation hole that extends through the rear surface of the handle portion, and wherein the first ventilation hole occupies at least approximately 5% of the front surface of the handle portion and the second ventilation hole occupies at least approximately 5% of the rear surface of the handle portion.

2. The dental hygiene device of claim 1, further comprising the interdental brush.

3. The dental hygiene device of claim 2, wherein the recess retains the interdental brush with a friction fit.

4. The dental hygiene device of claim 3, wherein the recess comprises a surface, the at least one interdental brush includes a grip, and wherein the surface of the recess and the grip are generally tapered so that the friction fit occurs at least between the surface of the recess and the grip.

5. The dental hygiene device of claim 2, wherein the connection portion comprises an opening adapted to hold the interdental brush with a friction fit.

6. The dental hygiene device of claim 2, wherein the interdental brush comprises a bristle portion, wherein the bristle portion is substantially aligned with a centroid of the first ventilation hole when the interdental brush is retained by the interdental brush storage portion.

7. The dental hygiene device of claim 2, wherein the interdental brush comprises a bristle portion, wherein the bristle portion is substantially aligned with a centroid of the second ventilation hole when the interdental brush is retained by the interdental brush storage portion.

8. The dental hygiene device of claim 2, wherein the interdental brush includes a bristle portion, the first ventilation hole includes a first centroid, and the second ventilation hole includes a second centroid, and wherein the bristle portion is substantially aligned with the first centroid and the second centroid when the interdental brush is retained by the interdental brush storage portion.

9. The dental hygiene device of claim 1, wherein the connection portion comprises two lobes generally equally spaced about the periphery of the connection portion.

10. The dental hygiene device of claim 1, further comprising a first grid component substantially covering the first ventilation hole.

11. A dental hygiene device comprising:
an interdental brush comprising a bristle portion; and
a toothbrush component comprising a brush portion, a neck portion, and a handle portion, the handle portion including a front surface, a rear surface, and an interdental brush storage portion, the interdental brush storage portion including a recess adapted to accommodate the interdental brush, a connection portion, and at least one ventilation hole in communication with the recess,
wherein the at least one ventilation hole includes a first ventilation hole with a first centroid that extends through the front surface of the handle portion and a second ventilation hole with a second centroid that extends through the rear surface of the handle portion;
wherein the recess retains the interdental brush with a friction fit, and wherein the connection portion comprises two lobes generally equally spaced about a periphery of the connection portion, and wherein the interdental brush includes a bristle portion where the bristle portion is substantially aligned with the first centroid and the second centroid.

* * * * *